United States Patent [19]

Villaveces

[11] Patent Number: 4,921,199

[45] Date of Patent: May 1, 1990

[54] DEVICE FOR AIDING IN PREPARATION OF INTRAVENOUS THERAPY

[76] Inventor: James W. Villaveces, 88 Fugenia Dr., Ventura, Calif. 93003

[21] Appl. No.: 268,427

[22] Filed: Nov. 8, 1988

Related U.S. Application Data

[63] Continuation-in-part of Ser. No. 185,963, Apr. 25, 1988, Pat. No. 4,852,844.

[51] Int. Cl.⁵ ............................................. A61M 5/32
[52] U.S. Cl. ................................ 248/314; 248/316.7; 604/192; 604/263
[58] Field of Search ............... 248/534, 537, 538, 539, 248/205.1, 205.3, 205.4, 205.2, 359 R, 108, 359 A, 360, DIG. 9, DIG. 16, 221.3, 221.4, 224.4, 312, 312.1, 313, 65, 74.1, 74.2, 309.1, 314, 316.1, 316.7, 121; 604/192, 187, 263; 206/365, 366, 380

[56] References Cited

U.S. PATENT DOCUMENTS

| | | | |
|---|---|---|---|
| 1,053,255 | 2/1913 | Ward | 248/538 |
| 2,459,692 | 1/1949 | Fletcher | 248/916 |
| 2,657,894 | 11/1953 | Slkenar | 248/221.4 |
| 3,203,653 | 8/1965 | Hall | 248/DIG. 9 |
| 3,304,039 | 2/1967 | Edelman | 248/108 |
| 3,370,818 | 2/1968 | Perr | 248/205.2 |
| 4,239,167 | 12/1980 | Lane | 248/205.3 |
| 4,375,849 | 3/1983 | Hanifl | 206/366 |
| 4,429,793 | 2/1984 | Ehmann | 206/366 |
| 4,485,918 | 12/1984 | Mayer | 206/380 |
| 4,573,576 | 3/1986 | Krol | 206/366 |
| 4,596,562 | 6/1986 | Vernon | 604/192 |
| 4,623,336 | 11/1986 | Pedicano | 604/263 |
| 4,717,386 | 1/1988 | Simmons | 604/263 |
| 4,737,149 | 4/1988 | Gillilan | 604/192 |
| 4,786,025 | 11/1988 | Shuman | 248/221.4 |

FOREIGN PATENT DOCUMENTS

| | | | |
|---|---|---|---|
| 2740335 | 9/1977 | Fed. Rep. of Germany | 206/366 |
| 3433359 | 4/1986 | Fed. Rep. of Germany | 604/263 |
| 2198644 | 6/1988 | United Kingdom | 604/192 |

Primary Examiner—Ramon O. Ramirez
Assistant Examiner—Robert A. Olson
Attorney, Agent, or Firm—Milton S. Gerstein

[57] ABSTRACT

A device for aiding a nurse in the preparation and set-up of intravenous therapy. The device has a backing plate with a backing layer of adhesive for securement to an IV pole, the backing plate being made of a flexible material so that it may be wrapped about the IV pole. A frustro-conical hollow member is supported by the front surface of the backing plate in which are provided friction-gripping ribs to firmly hold and grip a needle-cap of an intravenous needle, so that, when the needle and its cap are inserted into the hollow the cap is firmly held, after which the needle proper may be removed from the cap for subsequent IV therapy. The device allows a nurse to accomplish such needle and cap separation with only one hand, to free her other hand to hold another part of the IV set-up or to perform another task.

7 Claims, 5 Drawing Sheets

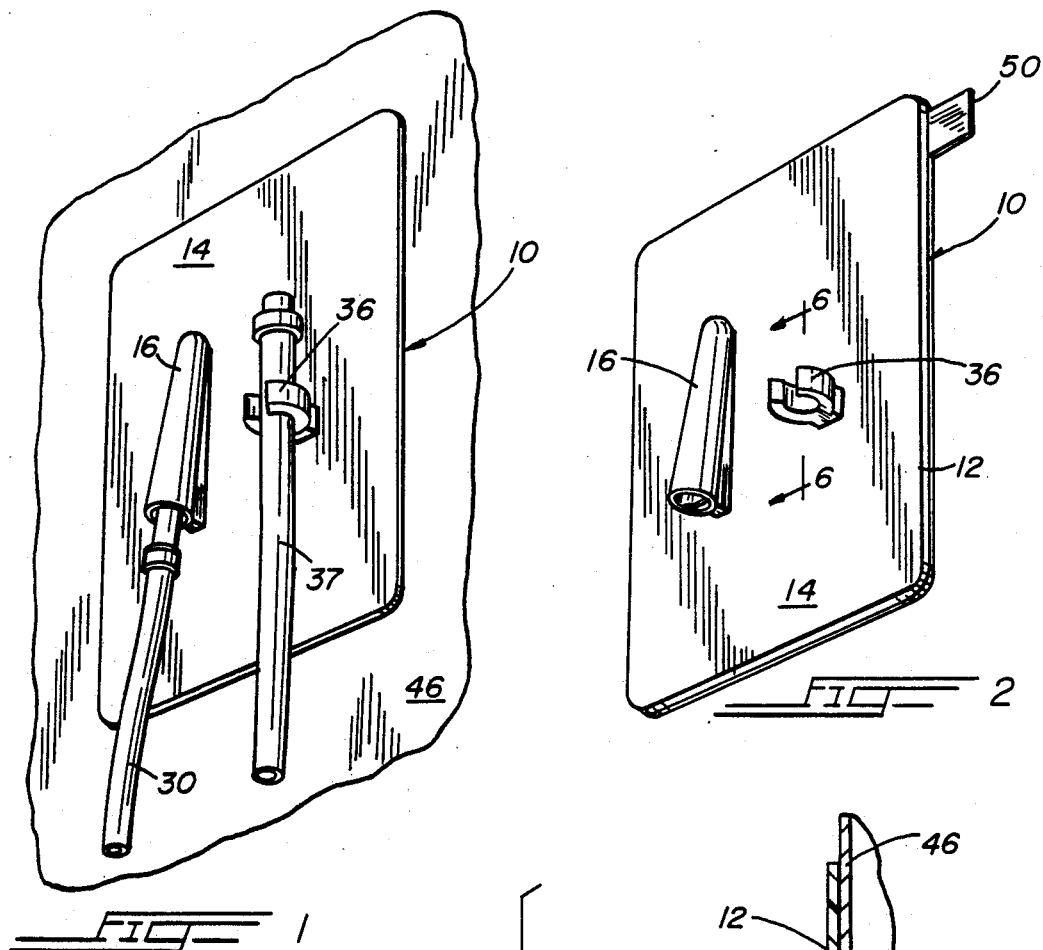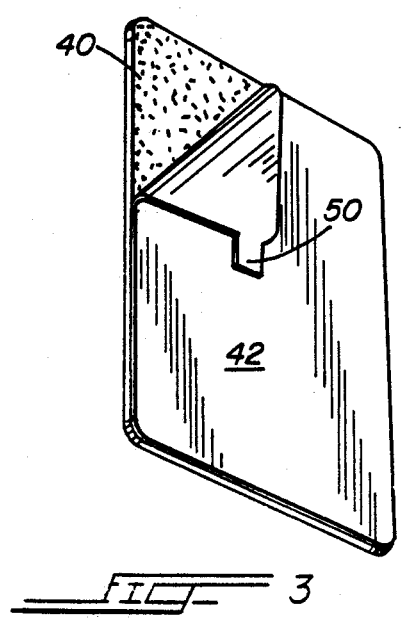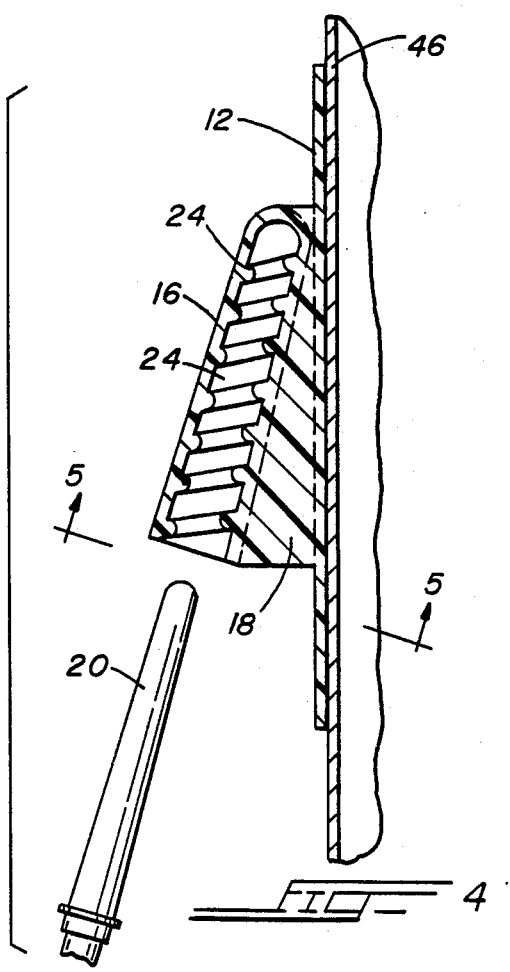

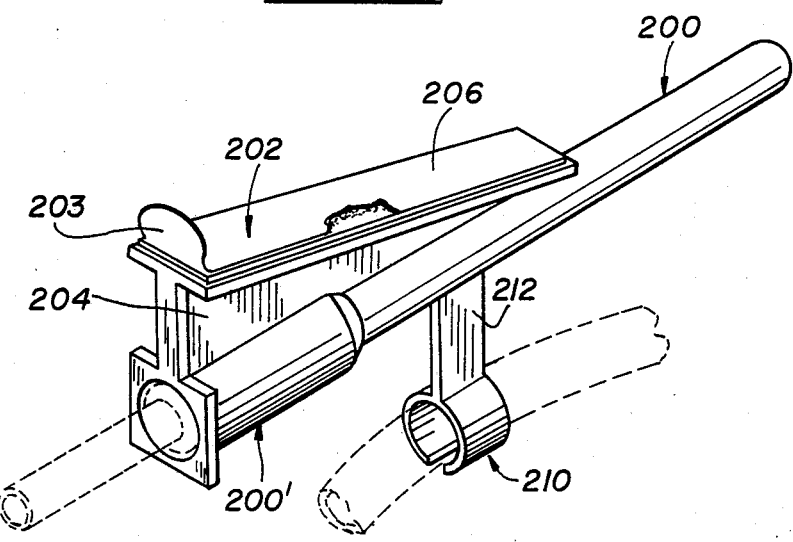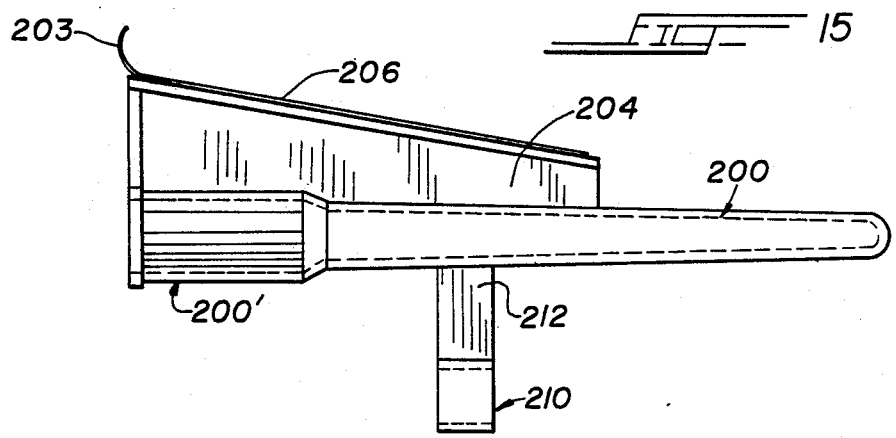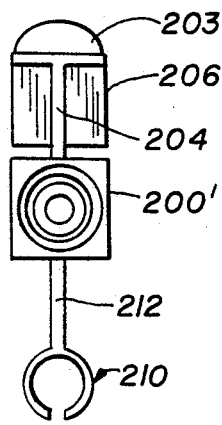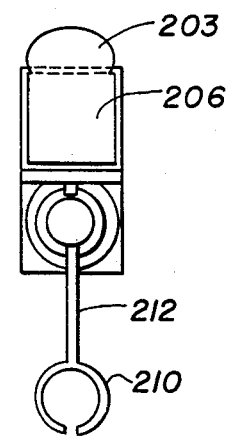

DEVICE FOR AIDING IN PREPARATION OF INTRAVENOUS THERAPY

CROSS-REFERENCE TO RELATED APPLICATION

This is a continuation-in-part of application Ser. No. 185,963, filed on Apr. 25, 1988, now U.S. Pat. No. 4,852,884.

BACKGROUND OF THE INVENTION

The present invention is directed to a device that aids a nurse in the preparation of setting up intravenous therapy. At least ten million of the more than forty million Americans hospitalized each year receive some form of intravenous therapy, such as blood transfusion, fluid and electrolyte replacement or total parental nutrition. Many things may go wrong with such therapy, such as, for example, sepsis. In effect, the IV is a conduit through the protective skin for an infection, which, therefore, must be guarded against. Any such tube inserted into the body, whether IV, nasogastric feeding, intra-arterial monitoring line or urinary catheter, deserves a maximum in antiseptic technique. Yet, proof is extant showing that hospital personnel are often delinquent in meeting necessary sanitary and hygienic precautions. Studies have found that 8% of nosocomial (hospital-acquired) infections are ascribed to use of intravascular lines. This translates into an estimated 50,000 device-related septisemias in the United States each year. Of 97 nosocomial epidemics in the world literature between 1965 and 1978, fully ⅓ derived from infusion therapy. Cultures done on catheter or needle used in IV therapy are positive for bacterial isolation in 33% of infusions during the first 12 hours of infusion. Studies have shown the link between thrombophlebitis in patients to the bacterial contamination which has been ascribed to non-aseptic techniques during cannula insertion. It is also a common problem to have nurses use unsanitary techniques in the handling of infiltrated IV lines and clot-blocked IV catheters, as well as catheter-bags needing emptying.

Nurses must set up IV solutions, lines, and needles, and to connect them all before attempting to insert the needle and cannula through the skin, and often have no assistants. Thus, they are forced to take short cuts because of time constraints. It is common for a nurse to remove the cap of a needle with her teeth, then reinsert the needle into the cap held between the teeth. Nurses are also wont to drop tubings, which are left to swing in the air, while the nurse clears a blocked line with a syringe, after which clearing, the tubing is reinserted in the needle or catheter. Ofttimes, the tubing is held under the armpit or draped over the IV pole while the needle or catheter is checked. The problem is, simply, that the nurse has too many tasks to perform in such a short time. She must hold the needle, syringe, tubing, caps and tape when the various IV procedures are undertaken. To replace the IV tubing everytime the line infiltrates or is blocked is not cost effective, which also leads to potential contamination at tubing-ends and cannula ends.

SUMMARY OF THE INVENTION

It is, therefore, the primary objective of the present invention to provide a device by means of which greater care and hygiene may be achieved during the setting up and administering of an intravenous unit as well as during the maintenance thereof.

It is an objective of the present invention to provide a unit that provides a location for use by a nurse when setting up intravenous feeding, and the like, that will temporary hold portions of the IV system, in order to free one of her hands in order to perform another task necessary for the IV installation, preparation, maintenance or removal.

It is an objective of the present invention to provide such a unit that, specifically, temporary holds the cap of the IV needle or catheter, and which may be used for removing the cap from the needle with the use of only one hand during initial IV installation.

It is an objective of the present invention to also provide such a unit that will hold the end of the IV tubing during initial set-up as well as during removal.

It is also an objective of the present invention to provide a high-density, foam-like block into which is inserted a used needle of an IV, which needle is used only to pierce through the skin for a small-diameter sleeve through which the IV fluid is passed to the body.

Toward these and other ends, the unit of the present invention, in a first embodiment, is a plate-like member having a backing of adhesive or a half of a hook-and-pile fastener, which backing or plate itself is flexible in order to wrap it around a conventional IV post or pole. The plate includes on its front surface face an angularly-mounted, conically-shaped, hollow tube into which is insertable an IV needle or catheter with its cover cap thereon. The interior surface of the hollow tube is provided with a spiral rib extending approximately the entire length of the tube, so that, upon the insertion of the needle and its cover cap into the conically-shaped hollow tube, the needle cover cap is held therein by the static friction provided via the spiral rib, so that the needle may be easily removed from the cover cap. The entire procedure of placing the needle and its cap into the tube and the removal of the needle therefrom and from its associated cap is accomplished with one hand, to thus free the the nurse's other hand for other needed tasks in setting up and preparing the IV, or the like. The front surface face of the plate is also provided with a C-clamp, or the like, for holding the end of the IV tubing with its attached cover for accomplishing the removal of that cover from the tube-end also by one hand. The C-clamp is also useful in temporarily holding any tube during set-up, maintenance, infiltration or withdrawal, such as feeding tubes, suction tubes, urine drainage tubes, and the like.

BRIEF DESCRIPTION OF THE DRAWING

The invention will be more readily understood with reference to the accompanying drawing, wherein:

FIG. 1 is an isometric view showing the device for aiding the preparation of intravenous therapy of the invention attached to a post or pole of an IV stand;

FIG. 2 is an isometric view thereof showing the device before securement to the pole;

FIG. 3 is a rear isometric view showing the peelable backing layer of the unit of the invention for exposing the adhesive for securement of the unit to an IV pole;

FIG. 4 is a longitudinal cross-sectional view of the frustro-conical holder for the removal of the needle-cap having a spiral-shaped interior rib for gripping a needle-cap;

FIG. 14 is an isometric view of another embodiment according to the invention with the backing plate being integrally formed with the IV needle cap, with a tube-holder integrally formed therewith;

FIG. 15 is a side elevation view thereof;

FIG. 16 is a front view thereof;

FIG. 17 is a rear view thereof;

DETAILED DESCRIPTION OF THE INVENTION

Figure 5:
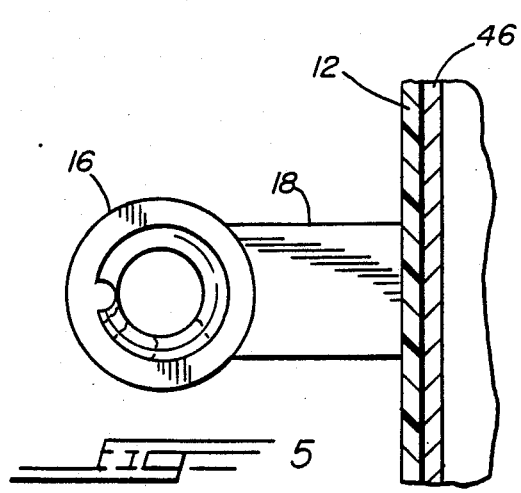
FIG. 5 is a view taken along line 5—5 of FIG. 4.
Figure 6:
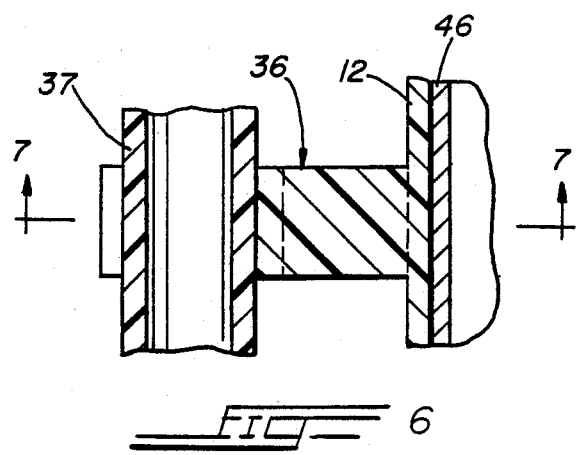
FIG. 6 is a view taken along line 6—6 of FIG. 2.

Referring now to the drawings in greater detail, the unit for aiding in the preparation of intravenous therapy is indicated generally by reference numeral 10. The unit 10 is preferably a disposable product, meant for use only one time or for one patient, after which it is discarded in a sanitary manner. The unit 10 is, therefore, made of any suitable flexible thermoplastic resin material, and is defined by a flat plate member 12 having a front planar surface 14 mounting a downwardly-extending, frustro-conically shaped, hollow, holding tubular element 16, having an open end facing downwardly for the passage therethrough of a needle-cap 20 shown in FIG. 4. The holding tubular element 16 forms an acute angle with respect to the front surface 14, as best seen in FIG. 4, so as to allow for easy insertion of the needle and its cap 20. The element 16 is formed integrally with the face plate 12 and connected to the front surface 14 via a web 18 seen in FIG. 4 that increases in width in the downward direction, in order to establish the acute angular positioning of the element 16. The interior circumferential surface of the element 16 is provided with a spiral rib 24 which provides gripping surfaces along the length of the element 16 by which the needle-cap 20 is gripped, so that after such gripping, the needle or catheter proper 26 (see FIG. 9) may be easily removed from its cap by simply pulling on the associated tubular connections 30 connected to the needle. Needle-caps are generally difficult to remove from its associated needle, manual removal being tedious, time-consuming, and difficult for an average nurse. The element 16 and its spiral rib allow such needle and cap separation to be carried out easily, quickly and with only one hand. The shape of the element 16 is preferably frustro-conical in order to conform to the frustro-conical shape of the needle-cap 20. Alternatively, the element 16 may be cylindrical, with the interior spiral rib forming an interior hollow frustro-conical volume, by having the rib portions thereof project more outwardly from the interior circumferential wall of the element 16 as the spiral progresses upwardly along the interior of the element 16. An additional alternative is simply using such a spiral tubing defining an interior frustro-conical volume that is connected to the front surface 14 via the web 18 directly. The unit 10 also has a C-clamp member 36 which is used to hold the end of an IV tubing, nasogastric tubing, intra-arterial monitoring tube line, urinary catheter tubing 37, and the like, which is used with the needle proper. The C-clamp is also used for holding the cap or cover of the IV tubing, so that the tube-end may be removed from its cap in a manner similar to the needle-cap remover member 16.

Figure 8:
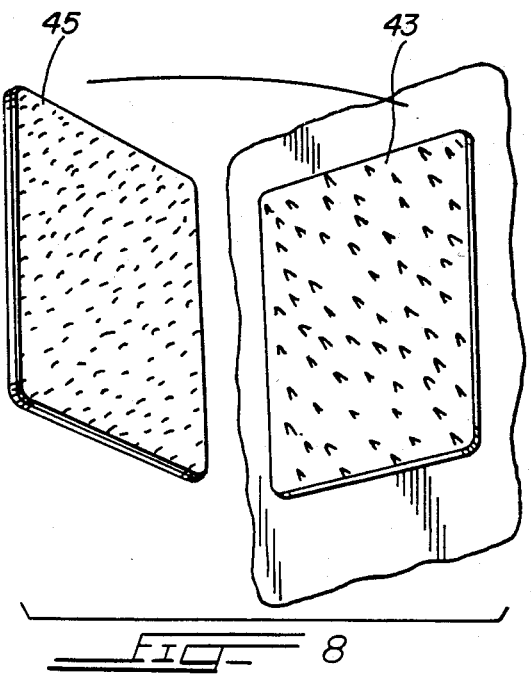
FIG. 8 is an isometric view showing the adhesive backing layer exposed after removal of the protective sheet.

The unit 10 is provided with an adhesive backing layer 40 that is exposed after a rear protective sheet 42 is removed. This adhesive layer is used for securing the unit 10 to a portion 46 IV pole or unit. Since a typical IV pole is relatively narrow, in the preferred embodiment, the plate 12 is made of a soft thermoplastic resin material that is conventional in order to allow the unit 10 to be wrapped around the outer circumferential surface of the IV pole, with the adhesive layer 40 consummating securement. Cardboard may also be used instead. Instead of the use of an adhesive backing, conventional hook-and-pile fasteners may be used, such having one portion 43 easily securable to the IV pole by a backing of adhesive, with the backing of the unit 10 having the mating portion 45 of the hook-and-pile fastener, as shown in FIG. 8. A tab 50 is also provided in order to allow for the easy peeling away of the protective sheet 42.

Figure 9:
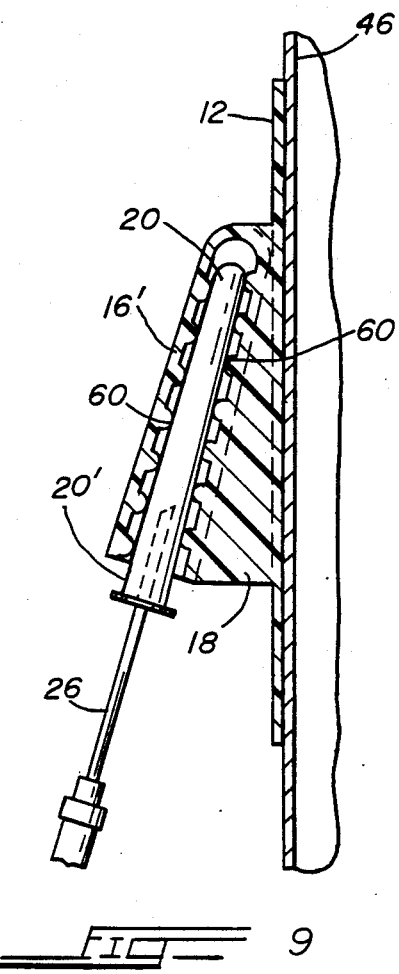
FIG. 9 is a modification of the unit of the invention with the frustro-conical holding tube for the needle-cap being provided with a plurality of interior protuberances for gripping the needle-cap.
Figure 7:
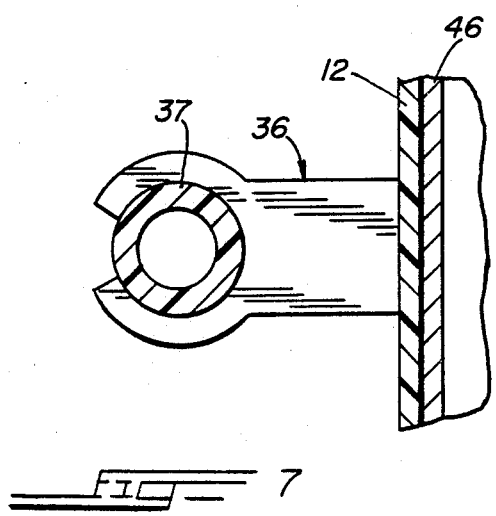
FIG. 7 is a cross-sectional view taken along line 7—7 of FIG. 6.

FIG. 9 shows a modification of the unit 10 in that the element 16' is the same as the element 16 of the preferred embodiment with the exception of the interior spiral rib having been replaced with simple radially-inwardly projecting beads 60 along the length of the frustro-conically shaped interior volume of the element 16' to provide the frictional gripping surfaces to hold the needle-cap 20. Each bead 60 may also, preferably, be circular.

Figure 10:
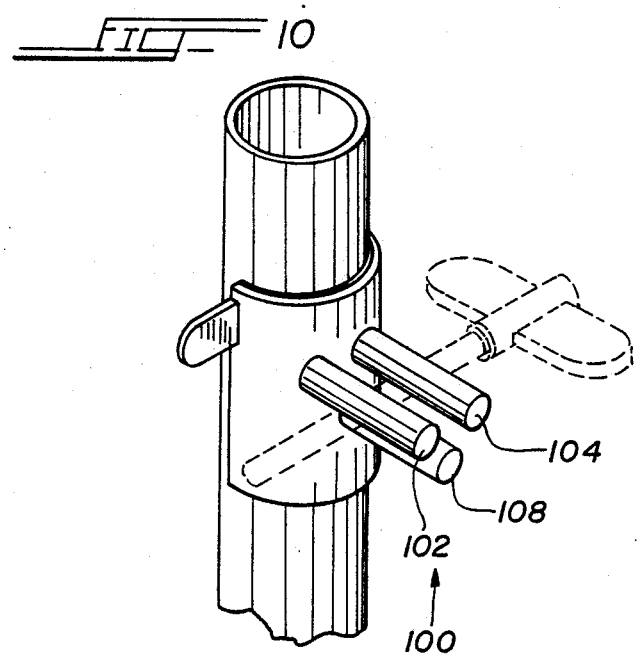
FIG. 10 is an isometric view of another embodiment of the invention used for pediatric butterfly needles.

It is, of course, possible to provide other friction-holding elements within the tubular element 16. such as internal, longitudinal, parallel ribs extending along the length of the tubular element 16. For pediatric caps, which are more tubular or cylindrical in shape, the tubular element 16 would also be substantially tubular or cylindrical in shape, with a chosen embodiment of internal friction-producing ribbing, and the like. Furthermore, for pediatric caps, instead of a cylindrical tubular element 16, the unit 100 shown in FIG. 10 may be used. The unit 100 shown includes the backing plate as in the other embodiments, but instead of the tubular element 16 for frictionally retaining the cap, a pair of bar members 102, 104 are provided. Positioned between these two bar members is an offset bar member 108. The tubular cap of the pediatric butterfly needle may therefore pass under each leg 102, 104 and above the bar 108, by which it is frictionally engaged and held.

Figure 11:
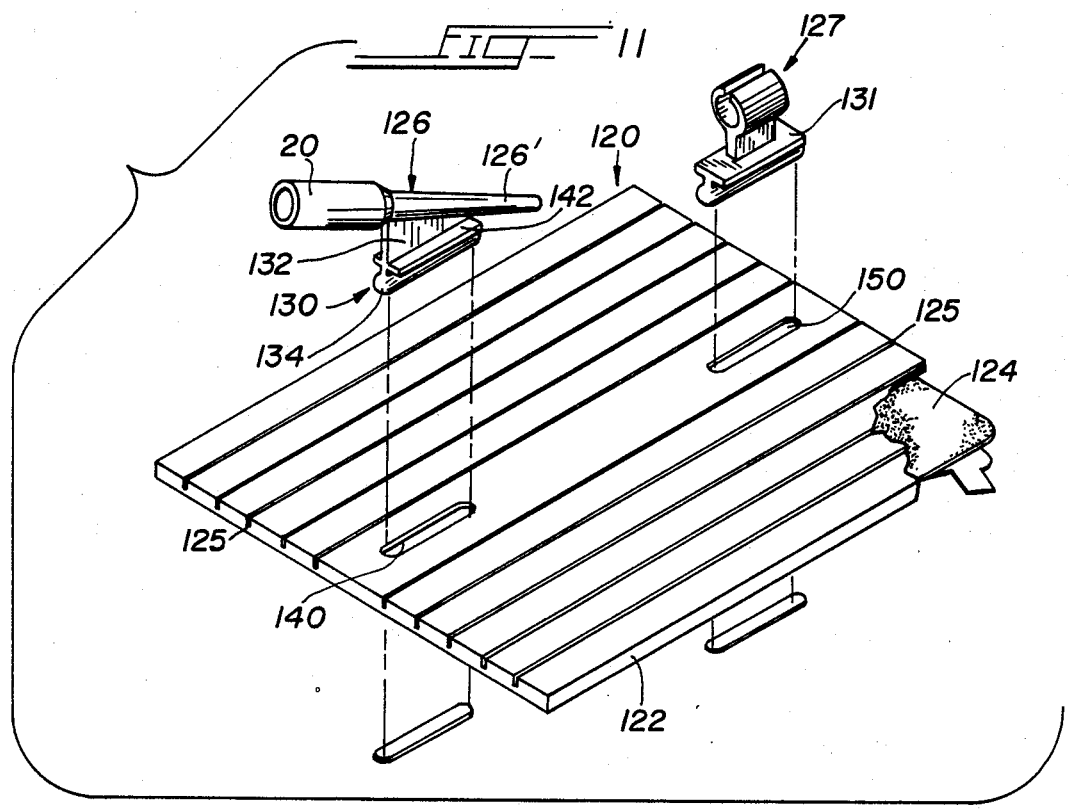
FIG. 11 is a modification of the embodiment of FIGS. 1-8 in which the backing plate is formed with a series of parallel grooves to allow for enhanced bending thereof for conforming to an IV pole, with the tube-holder and needle-cap remover being snap-fitted to the backing plate, for backing plates of relatively substantial thickness.
Figure 12:
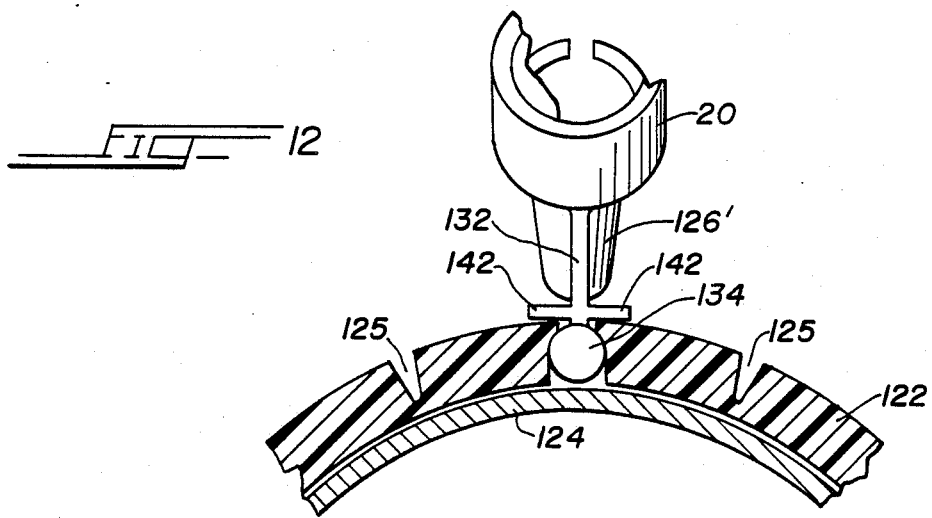
FIG. 12 is a partial cross-sectional detail view thereof showing the needle-holder.
Figure 13:
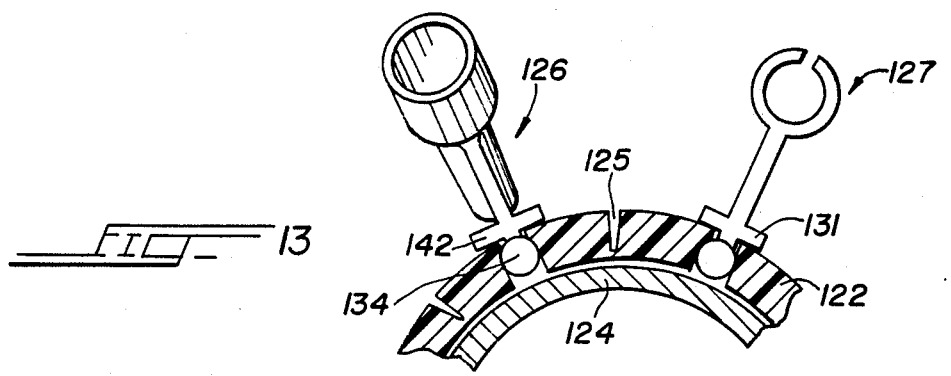
FIG. 13 is a transverse cross-sectional view.

FIGS. 11-13 show yet another embodiment of the invention, which is designed to ensure strength to the unit but ease of flexibility so as to be bent about an IV pole, or the like. The unit 120 has a backing plate 122 that is relatively thick. A rear adhesive layer 124 allows securement of the unit to the IV pole. A series of parallel transverse U-shaped or V-shaped grooves or ridges 125 are formed in the front-surface face of the backing plate, which backing plate is preferably made of hard, thermoplastic resin material. These grooves allow the backing plate to be flexible and to bend about the IV pole, even though the plate itself is relatively thick. This allows for such a thick plate to be used, in order to add structural integrity and strength to the unit, and at the same time allow for the plate to be manufactured more easily with the cap-remover and tube-clamp injection-molded therewith. Alternatively, the cap-remover 126 and tube-holder 130 are assembled to the backing plate 122, as shown in FIGS. 11-13. The needle cap-remover 126 is provided with a downwardly-extending retaining element 130 having a trapezoidal-shaped connecting web 132, like ramp 18 of FIG. 1, at the bottom of which is provided a retaining cylinder or elongated bead 134 for insertion into an elongated slot 140 formed in the backing plate 122. The retaining cylinder 134 has a length substantially equal to the length of the slot 140, and a lateral dimension greater than the width of the slot 140, so that it is force-fitted through the slot 140. A pair of horizontal fins 142 prevent the complete passage of the web 132 through the slot, whereby the needle-cap remover 126 is firmly mounted to the backing plate, in a manner best seen in FIGS. 12 and 13. The tube-holder 130 is similarly mounted to a slot 150 formed in the backing plate, which slot 150 is offset from the slot 140, so that the cap-remover 126 and tube-holder 130 do not lie in the same plane, as shown in FIG. 13. In the version shown in FIGS. 11-13, the backing plate is ridged, as described above, with the cap-remover and tube-holder snap-fitted. However, in practice, when the backing plate is made with the series of ridges or grooves 126, the remover and holder may be formed integrally with the backing plate, as by injection molding, the backing plate 122 being of a relatively large thickness. However, when making the backing plate of relatively thin, in order to provide inherent flexibility, the ridges or grooves 122 are not necessary. In this case, when using a thin backing plate, the snap-fitting remover 126 and holder 130 are used, since, during manufacture, the backing plate is formed by punching out a thin plate from a stock, after which the slots 140, 150 are formed, and the remover and holder snap-fitted therein. The cap-remover proper 126', like the member 16, may be provided with interior friction-generating members, as in the previous embodiments. However, as long as the slope of the walls of the frustro-conical shaped member 16 or 126' is less than seven degrees, then ample retaining friction is created by the smooth walls of the member 16, 126' itself, so that no additional friction-generating parts need be incorporated in the interior thereof.

The plate 122 may be provided with a plurality of slots 140 so that a plurality of needle cap-removers 126 may be provided, such as in two rows of three removers. This allows for multiple use of the same device. This also has especial use in anesthesia induction, which requires one hand over the patient's mask and one hand holding the anesthesia syringe. In addition, in order to allow for more easy aiming of the needle cap into the remover, the mouth of the cap remover may be enlarged via a larger conical member, or funnel-like member, to provide an easier insertion of the cap into the remover.

An alternative version of the present invention is shown in FIGS. 14-17 where the needle-cap itself is provided with the adhesive strip or a portion of a hook-and-pile fastener by which the needle-cap 20 itself is secured to the IV pole directly via such securement. In this case, the needle-cap 200 has a rectangular strip 202, with tab 203, of such securing means is fixedly attached to an outer circumferential surface portion of a ramp plate 204 formed integrally with the cap 200 proper, the outward surface of the strip having the adhesive or portion of the hook-and-pile fastener thereof. The cap 200 may be reinforced, if needed, by a larger-diameter, forward section 200'. The IV needle or catheter, shown in dotted in FIG. 14, is received in the hollow interior of the cap 200, in the usual manner. In use, the needle-cap itself is attached to the IV pole, or the like, by peeling back the protective layer 206, and securing it to the IV pole, and, thereafter, pulling the needle out of the cap 200, with the cap 200 remaining attached to the IV pole, for subsequent re-insertion of the needle. Projecting downwardly from an end portion of the ramp plate cap 200 is a tube-holder 210 and integrally formed therewith, via connecting web 212, with the tube holder 210 being spaced below the the cap proper 200, so that the tube of the IV unit may be placed and retained therein, as explained above.

Figure 18:
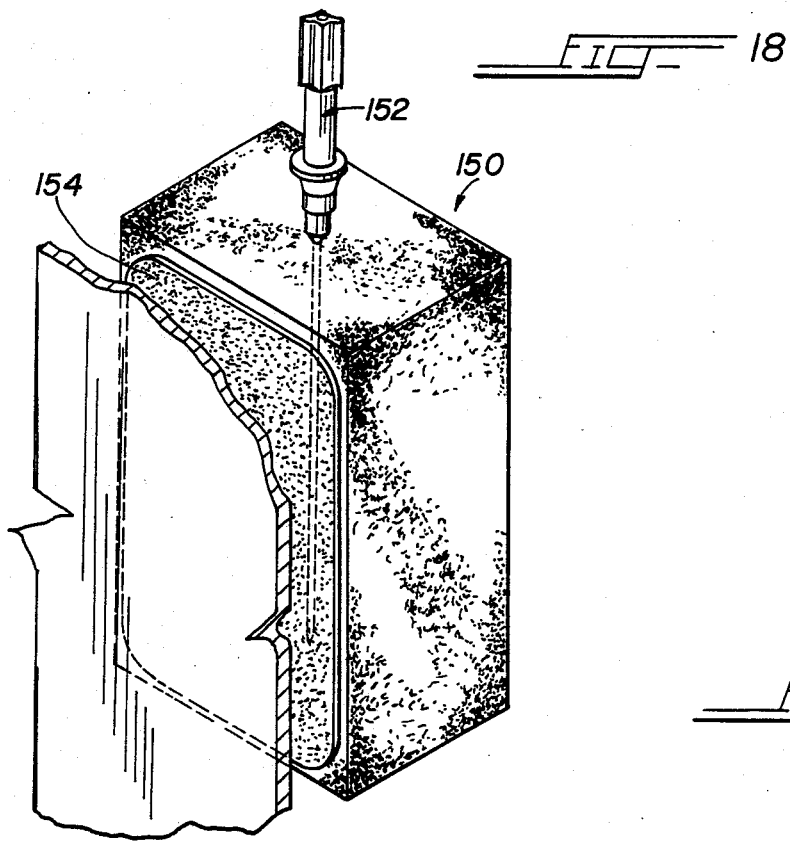
FIG. 18 is an isometric view of a high-quality foam block according to the invention into which a used needle is inserted, for preventing contamination.
Figure 19:
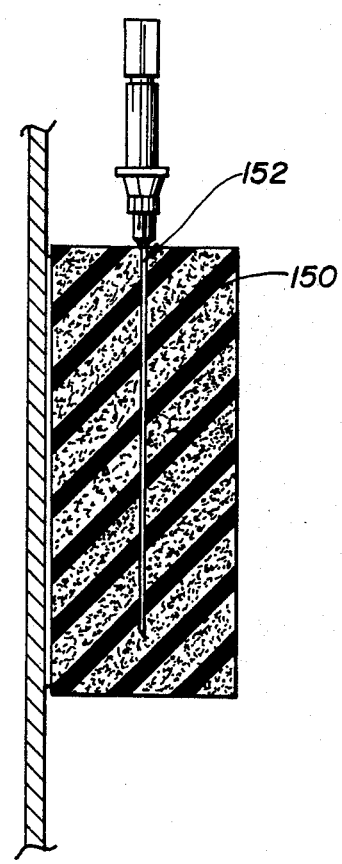
FIG. 19 is a transverse cross-sectional view thereof.

Referring now to FIGS. 18-19, there is shown a block of high-density styrofoam 150 for use in receiving a used needle or catheter, in order to prevent such used needle from contacting people. In particular, the needle 152 is that used for piercing the skin of a patient being readied for receiving IV treatment. The needle 152, generally called an intercatheter needle, is immediately removed after piercing the skin, so that the plastic needle-sleeve in which the needle is positioned may enter the pierced opening, for subsequent intravenous therapy. The block is preferably between 3-4 inches in height, and one inch square in cross section. The block 150 comes with an adhesive backing layer 154 for securing it to an IV pole, night stand, or the like. The block, after the intercatheter needle has been inserted, may then be thrown away with other contaminants. It is intended that the styrofoam block 152 be packaged with the needle cap-remover and tube-holder embodiments described above.

While a specific embodiment of the invention has been shown and described, it is to be understood that numerous changes and modifications may be made therein without departing the scope and spirit of the invention as set forth in the appended claims. The adhesive backings may also be secured to a flat surface, such as a mayo stand. Also, the angle of slope of the cap remover or tube holder is preferably either 30 or 45 degrees sloping upwardly, so that the opening is at the top and the needle or cap inserted downwardly.

What I claim is:

1. A device for aiding a nurse, or the like, in the preparation of intravenous therapy, and the like, comprising:
   a backing plate having a substantially planar front surface and rear surface;
   at least one means for holding and gripping a needle-cap mounted on said front surface defining a hollow interior into which a needle-cap may be inserted;
   said rear surface of said backing plate having securing means thereon for attaching said backing plate to an IV pole, and the like, whereby a needle with its cap may be inserted into said means for holding and gripping to grip the needle-cap, after which the needle proper may be removed from its cap for use in intravenous therapy;

said backing plate being a thin plate that is flexible for wrapping about an IV pole or the like, said backing plate further comprising at least one elongated substantially linear slot formed in said front surface and extending rearwardly to at least a depth directly juxtapositioned adjacent said rear surface; means for mounting said means for holding and gripping to said backing plate, said means for mounting comprising an elongated substantially linear retaining bead member forcibly insertable into said slot, and web means interconnecting said bead member to said means for holding and gripping, whereby said thin plate is stamped out from stock to provide a very thin and flexible member, with said means for holding and gripping thereafter being mounted to said thin plate; said means for mounting also comprising means for limiting entrance of said bead member past a pre-selected insertion.

2. The device according to claim 1, further comprising means for holding a tube-end also mounted on said front surface of said backing plate, said backing plate comprising another slot for receiving therein a portion of said means for holding a tube-end, said means for holding a tube-end comprising tube-receiving means, a retainer bead for forced insertion in said another slot, and flange means for limiting the forced insertion of said retainer bead into said another slot, said whereby said means for holding a tube-end is mounted to said backing plate; said slots of said backing plate being separated a specified distance apart.

3. The device according to claim 1, wherein said means for holding and gripping comprises a hollow member having a slope of the interior surface thereof of less than 7 degrees, said interior surface being smooth and unbroken.

4. In a new and unused intravenous-type needle comprising a needle proper for penetration through and insertion into a portion of a human being, and an elongated protective closure cap, said elongated closure cap member defining a hollow interior into which is insertable said needle proper, the improvement comprising:

web means integrally connected to a portion of said protective closure cap member, said web means defining a flat upper outer surface and comprising a securing means on said flat outer surface for releasably attaching said cap member to a IV pole, or the like, a tube-end holding means for releasably securing an end portion of an IV tube thereto, and means for connecting said tube-end holding means to another portion of said protective cap member.

5. The improvement according to claim 4, wherein said web increases in width along the length thereof so that said outer flat surface slopes at an acute angle, so that when said cap is attached to an IV pole, it projects at an angle with respect to the vertical plate thereof.

6. The improvement according to claim 4, wherein said another portion of said cap member is diametrically opposite said portion to which said web means is connected, said tube-end holding means projecting from said cap member in a direction opposite to the projection of said web means from said cap member.

7. The improvement according to claim 4, in combination with an intravenous tube, said tube-end holding means holding an end portion of said intravenous tube.

* * * * *